United States Patent [19]

Wang et al.

[11] Patent Number: 5,412,112

[45] Date of Patent: May 2, 1995

[54] DERIVATIVES AND PREPARATION OF 2,2-DIMETHYL-5-SUBSTITUTED PHENOXY-PENTANOIC ACIDS

[75] Inventors: Hui-Po Wang; On Lee, both of Taipei; Chin-Tsai Fan, Tainan, all of Taiwan, Prov. of China

[73] Assignee: Industrial Technology Research Institute, Hsinchu, Taiwan, Prov. of China

[21] Appl. No.: 259,537

[22] Filed: Jun. 14, 1994

[51] Int. Cl.$^6$ .................. C07D 305/12; C07C 69/76; C07C 59/48

[52] U.S. Cl. .................. 549/328; 549/329; 560/61; 560/60; 562/470; 562/471

[58] Field of Search .................. 549/328, 329; 560/61, 560/60; 562/470, 471

[56] References Cited

U.S. PATENT DOCUMENTS

| | | | |
|---|---|---|---|
| 3,344,168 | 9/1967 | Galimberti | 560/61 |
| 3,474,095 | 10/1969 | Marchetti | 560/61 |
| 3,674,836 | 7/1972 | Creger | 560/61 |
| 3,707,566 | 12/1972 | Creger et al. | 260/613 D |
| 4,665,226 | 5/1987 | Kearney | 562/471 |
| 4,739,101 | 4/1988 | Bourgogne | 560/61 |
| 5,302,751 | 4/1994 | Marimaran | 562/401 |
| 5,310,757 | 5/1994 | Laruelle | 560/61 |

FOREIGN PATENT DOCUMENTS

| | | |
|---|---|---|
| 2207236 | 9/1987 | Japan . |
| 3104939 | 5/1988 | Japan . |
| 91/07373 | 5/1991 | WIPO . |

OTHER PUBLICATIONS

Morishita et al., "Synthesis and Hypolipidemic Activity of 2-Substituted Isobutyric Acid Derivatives", J. Med. Chem. 31:1205–1209, (1988).

Sircar et al., "Phenylenebis(oxy)bis[2,2-dimethylpentanoic acid]s: Agents that Elevate High $\alpha$ Density Lipoproteins", J. Med. Chem. 26:1020–1027, (1983).

*Primary Examiner*—Paul J. Killos
*Attorney, Agent, or Firm*—Fish & Richardson

[57] ABSTRACT

Novel 3-substituted derivatives of 2,2-dimethyl-5-substituted phenoxy-pentanoic acids of formula (I) are prepared. These compounds are prepared from 2,2-dimethyl-5-substituted phenoxy-3-hydroxy-pentanoic acid-$\beta$-lactones (formula II). The $\beta$-lactones are prepared by condensing relevant phenoxypropanals with dimethylketene.

12 Claims, No Drawings

DERIVATIVES AND PREPARATION OF 2,2-DIMETHYL-5-SUBSTITUTED PHENOXY-PENTANOIC ACIDS

BACKGROUND

The present invention relates to the derivatives of 2,2-dimethyl-5-substituted phenoxy-pentanoic acid, and in particular to the 3-substituted derivatives of 2,2-dimethyl-5-substituted phenoxy-pentanoic acid and the process of preparing the same and the intermidates thereof.

Substituted phenoxyalkanoic acids, for example the compounds represented by formulas (V) and (Va) below have been shown to be effective as hypolipoproteinemic agents.

According to U.S. Pat. No. 3,674,836 issued to Paul L. Creger and U.S. Pat. No. 3,707,566 issued to Paul L. Creger et al and J. Med. Chem. 31, 1207(1988), compound (V) may be prepared by the following scheme A.

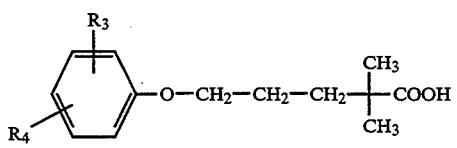
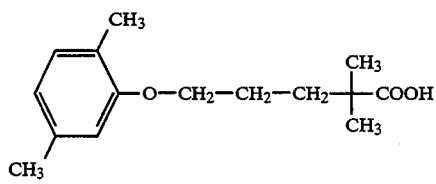

R = —COONa
  —COOR$_1$
  —CN
  —CHO
  —CH=N—R$_2$

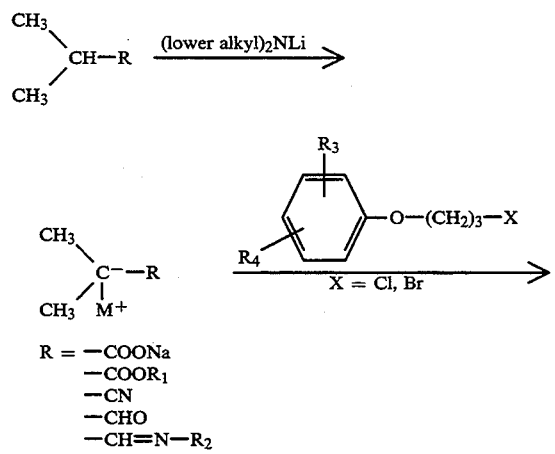

According to U.S. Pat. No. 4,665,226 issued to Francis R. Kearney, and J. Med. Chem. 30, 1816(1987), the compound (V) may also be prepared by the following reaction scheme B.

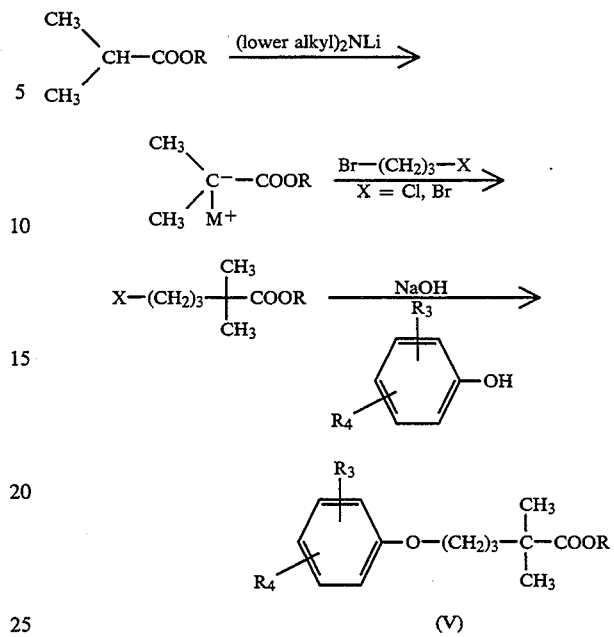

Both the above two processes for preparing compounds (V) were carried out in anhydrous condition at lower temperature with the introduction of inert gas, and involved the use of alkali metal salts of secondary amine. Accordingly, the preparation of compounds (V) according to the above mentioned processes require critical anhydrous reaction conditions with complicated procedures and apparatus in production scale. Moreover, the hazardous alkali metal salts must be handled with care and therefore are not suitable for scaling up production in industry.

SUMMARY OF THE INVENTION

The primary objective of the present invention is to provide a process for the preparation of derivatives of 2,2-dimethyl-5-substituted phenoxy-pentanoic acids, with the benefit in eliminating the aforementioned disadvantages.

The secondary objective of the invention is to present the invention of novel 3-substituted derivatives of 2,2-dimethyl-5-substituted phenoxy-pentanoic acids.

According to the invention, the derivatives of 2,2-dimethyl-5-substituted phenoxy-pentanoic acids are prepared from 2,2-dimethyl-5-substituted phenoxy-3-hydroxy-pentanoic acid-β-lactones. The novel β-lactones are prepared by condensing relevant phenoxypropanals with dimethylketene.

In the case of preparing the derivatives of 2,2-dimethyl-5-substituted phenoxy-pentanoic acids in which 3-position is hydrogen, 2,2-dimethyl-5-substituted phenoxy-3-hydroxy-pentanoic acid-β-lactones are subjected to hydrogenation in a polar protic solvent or polar aprotic solvent at a temperature of 20°–160° C. under 1–200 atm of hydrogen in the presence of Raney nickel, palladium on charcoal, or palladium hydroxide on charcoal.

In the case of preparing the derivatives of 2,2-dimethyl-5-substituted phenoxy-pentanoic acids in which 3-position is hydroxy or halogen, 2,2-dimethyl-5-substituted phenoxy-3-hydroxy-pentanoic acid-β-lactones are allowed to react with water, lower alkanol or hydrogen halide in aliphatic alcohol, aromatic olefin, or a polar aprotic solvent.

The present invention can be better understood with the subsequent description in detail and examples.

DETAILED DESCRIPTION OF THE INVENTION

In accordance with the invention, the compound of the invention, that is, the compound of formular (I):

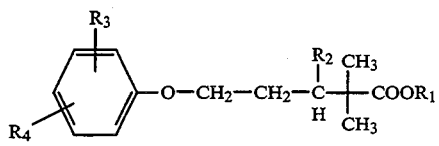
(I)

in which $R_1$ is hydrogen or $C_{1-8}$ alkyl;

$R_2$ is hydroxy or halogen; and $R_3$ and $R_4$ are respectively hydrogen, hydroxy, halogen, $C_{1-8}$ alkyl, $C_{1-8}$ alkoxy or $C_{1-8}$ acyl. can be produced by reacting a compound of formula (II):

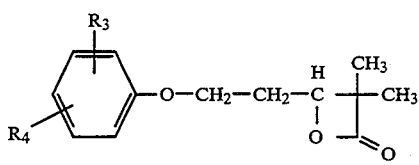
(II)

with water, lower alkanol or hydrogen halide in an appropriate solvent, for example aliphatic alcohol such as propanol or n-butanol, alkyl aromatics such as toluene or xylene and polar aprotic solvent such as dimethylformamide, dimethylacetamide. The reaction is usually carried out at a temperature of $-10°$ C. to $150°$ C. for 2–48 hours. The reaction can be summarized in the following reaction schemes (C):

charcoal can produce the compounds of formula (V) or (Va). Examples of the polar protic solvent suitable for use in this hydrogenation are acetic acid, and lower alkanol etc. Examples of the polar aprotic solvent suitable for use in this hydrogenation are tetrahydrofuran, 1,2-dimethoxyethane etc.

The 2,2-dimethyl-5-substituted phenoxy-3-hydroxypentanoic acid-$\beta$-lactones employed as starting materials in the foregoing processes can be prepared by reacting a compound of formula (III):

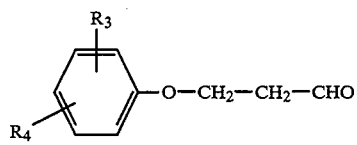
(III)

in which $R_3$ and $R_4$ are respectively hydrogen, hydroxy, halogen, $C_{1-8}$ alkyl, $C_{1-8}$ alkoxy or $C_{1-8}$ acyl, with dimethylketene of formula (IV):

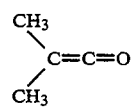
(IV)

in the presence of a lewis acid such as hydrogen chloride, zinc chloride, aluminum chloride, ferric chloride, titanium chloride, boric acid, and boron trifluoride. This reaction is carried out in nonpolar aprotic solvent such as tetrahydrofuran, diethylether, 1,2-dimethoxyethane or polar aprotic solvent such as hexamethylphospho-triamide. The reaction can be represented by the following reaction scheme (D).

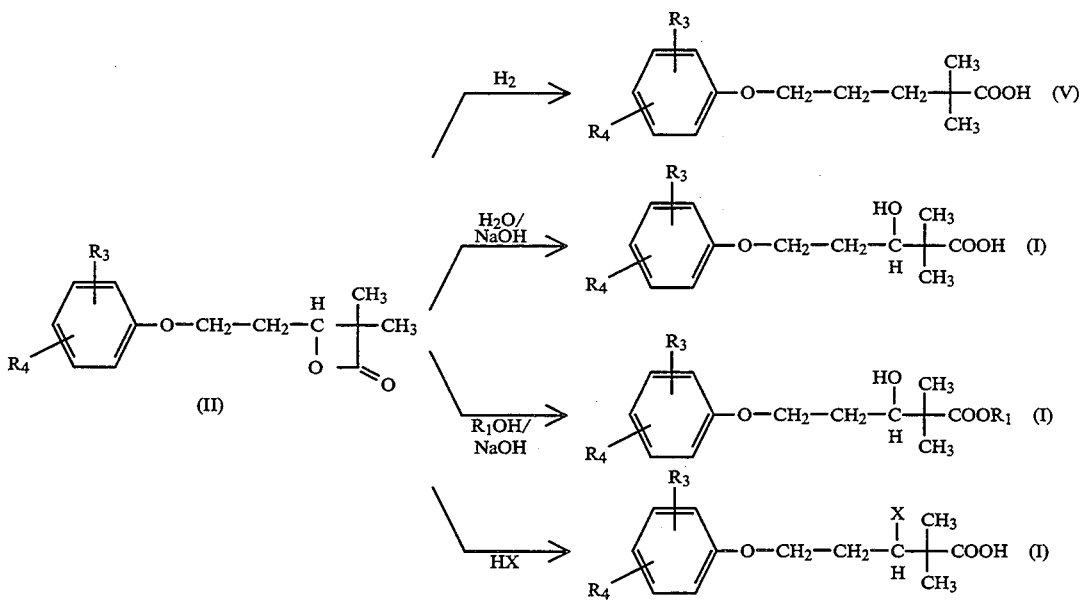

According to the invention, hydrogenation of the compound of formula (II) in a polar protic solvent or a polar aprotic solvent under 1–200 atm of hydrogen at a temperature of 20°–160° C. in the presence of Raney nickel, Palladium/charcoal or palladium hydroxide/-

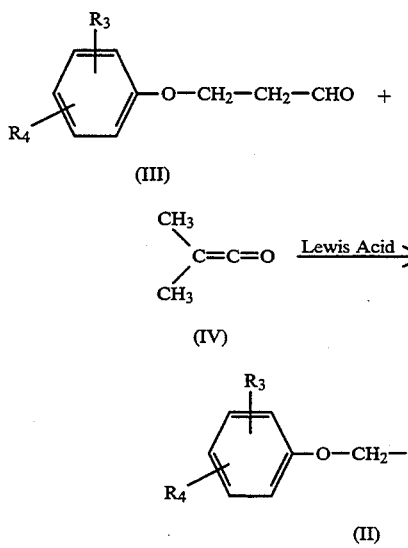

(III)

(IV)

(II)

The dimethylketene of formula (IV) is a monomer commonly used in synthesis of polymers. The propanals of formula (III) can be readily prepared by state-of-art organic synthetic methods.

The invention is illustrated by the following examples. Note that these examples are merely illustrative of the process of the invention and should not be treated as a limited scope of the invention defined in the appended claims.

EXAMPLE 1

Preparation of 2,2-Dimethyl-5-(2,5-dimethylphenoxy)-3-hydroxy-pentanoic Acid β-lactone To 0.56 g(0.003 mole) of 3-(2,5-dimethylphenoxy)-propanal in 10 ml of tetrahydrofuran, 0.02 g of $BF_3\cdot Et_2O$ and 0.21 g of dimethylketene were added, stirred at room temperature for 36 hours. The resulting solution was concentrated in vacuo and the residue was chromatographed to provide 0.56 g of the product, mp 80°–81° C. The yield was 75%.

PMR(80 MHz, $CDCl_3$): δ7.06(1H,d,Ar—H), 6.78(2H,d,Ar—H), 4.79(1H,t,O—CH), 4.14(2H,t,O—$CH_2$—), 2.42(3H,s,Ar—$CH_3$), δ2.3(3H,s,Ar—$CH_3$), 2.2(2H,q,$CH_2$—), 1.37(6H,s,—C—($CH_3$)$_2$—COO—).

EXAMPLE 2

Preparation of 5-(4-Chlorophenoxy)-2,2-dimethyl-3-hydroxypentanoic Acid β-lactone 3-(4-Chlorophenoxy) propanal (0.74 g, 4 mmol) was dissolved in 20 ml of ethyl acetate. $ZnCl_2$ (0.4 mmole), dimethylketene (0.28 g, 4 mmole) were added. The mixture was allowed to react at 4° C. for 48 hours. Evaporation and purification by chromatography gave 0.91 g (89%) of product as a liquid.

PMR(80 MHz, $CDCl_3$): δ7.07, 7.00,6.74,6.61(3H, m,Ar—H); 4.35, 4.22, (1H,d,—COO—CH—); 3.91, 3.85 (2H ,d,Ar—)—$CH_2$—); 2.6–2.0(1H, m, —$CH_2$—CH($CH_3$)—$CH_2$—); 2.41 (3H,s,Ar—$CH_3$); 2.32(3H,s,Ar—$CH_3$); 1.45–1.05(9H,m,other—$CH_3$). Mass M/z (rel, inten.): 262(18, M+), 135(6), 122(100), 97(50), 70(20), 55(30). IR(KBr): 3072–2881, 1827(vC=C), 1614, 1585, 1511, 1473,1465, 1430, 1404, 1394.

EXAMPLE 3

Preparation of 2,2-Dimethyl-5-(2,5dimethyl-5-(2,5-dimethylphenoxy)-pentanoic Acid (Gemfibrozil)

2,2-Dimethyl-5-(2,5-dimethylphenoxy)-3-hydroxypentanoic Acid β-lactone, 0.25 g, was dissolved in 50 ml of acetic acid. 0.01 g of Raney Ni was then added and allowed for hydrogenolysis at 70° C. under 11 atm of hydrogen for 48 hours. The mixture was filtered to remove Raney Ni and then evaporated in vacuo to remove acetic acid. The residue was dissolved in 50 ml of n-hexane, washed with 20 ml of water twice and extracted with 1M aqueous solution of sodium carbonate. The combined sodium carbonate solution was acidified with 2M hydrochloride solution and extracted with 20 ml of dichlormethane twice. The dichloromethane solution was then dried, filtered, and evaporated to dryness to provide 0.2 g of an oily liquid. The yield was 80%. Recrystallization from n-hexane gave the desired product as a solid, mp: 60°–60.5° C.

PMR(80 MHz, $CDCl_3$): δ9.75(1H, broad, —COOH); 7.06, 6.96, 6.61 (3H, m, Ar—H); 3.94(2H,s,Ar—O—$CH_2$—); 2.31 (3H, s,Ar—$CH_3$); 2.19(3H,s,Ar—$CH_3$); 1.79, 1.75 (4H, d—, Ar—O—$CH_2$—$CH_2$—); 1.26 (6H, s,C($CH_3$)$_2$—COO—).

EXAMPLE 4

Preparation of 2,2-Dimethyl-5-(2,5-dimethylphenoxy)-3-hydroxypentanoic Acid 2,2-Dimethyl-5-(2,5-dimethylphenoxy)-3-hydroxypentanoic acid-β-lactone, 1.24 g(5 mmole), was dissolved in 30 ml of methanol, and 10 ml of 2M sodium hydroxide was added. The resulting solution was heated to reflux for 72 hours. Acetic acid, 1.5 cc, was then added and evaporated to remove methanol. The crude product was partitioned between 20 ml of water and 15 ml of dichloromethane twice. The combined dichloromethane layers was washed with 30 ml of saturated NaCl solution, dried over anhydrous magnesium sulfate, and filtered. The filtrate was evaporated in vacuo to remove dichloromethane to give 1.04 g of solid product, mp 100°–100.5° C. The yield was 72%.

PMR (80 MHz, $CDCl_3$): δ7.03, 6.93 (1H,d,Ar, H); 6.68, 6.63 (2H, s,Ar—H); 6.45 (2H, broad, —COOH, —OH); 4.14 (2H, t, Ar—O—$CH_2$—); 4.00(1H,dd, —CH-(OH)—); 2.30(3H,s,Ar—$CH_3$); 2.16(3H,s,Ar—$CH_3$); 1.70 (2H,m, Ar, O, $CH_2$—$CH_2$—); 1.27, 1.25(6H,d,—C($CH_3$)$_2$—COO—). IR (kbR): 3446–2400 (bROAD), 1698 (vC=C), 1510 cm. Mass m/z (rel. inten.): 266(70, M+), 203(15), 179(15), 161(51) 145(32), 135(36), 127(11), 122(100), 107(45), 99(32), 88(21), 77(22), 71(23).

EXAMPLE 5

Preparation of Methyl 2,2-dimethyl-5-(2,5-dimethylphenoxy)-3-hydroxy-pentanoate

A solution of 2,2-Dimethyl-5-(2,5-dimethylphenoxy)-3-hydroxypentanoic acid-β-lactane, 0.49 g( 2 mmole ), and 4 mg(0.1mmole ) of sodium hydroxide was stirred in room temperature for 24 hours. Methanol was removed in vacuo. The residue was partitioned between 50 ml of EtOAc and 20 ml of a 1M sodium carbonate solution twice. The combined EtOAc layer was washed with 20 ml of saturated NaCl solution and dried over magnesium sulfate and filtered. The filtrate was evaporated in vacuo to dryness to give 0.25 g of the product as a liquid. The yield was 93%. Recrystallization from n-hexane gave the desired product as a solid, mp 40.5°–41° C.

PMR (80 MHz,CDCl$_3$); $\delta$7.02, 6.99(1H, d,Ar—H); 6.64(2H,s,Ar—H); 4.12(2H,t , Ar—O—CH$_2$—); 3.98(1H, dt,CH(OH)—); 3.69(3H, s,—COO—CH$_3$); 2.85( 1H,s,—OH); 2.30(3H,s ,Ar—CH$_3$); 2.17(3H,s,Ar—CH$_3$); 1.91 (2H, m, Ar—O—CH$_2$—CH$_2$—); 1.23 (6H,s,c(CH$_3$)$_2$—COO—).

IR(KBr): 2977,2937, 1733 (vC=C), 1703, 1510 cm Mass m/z (rel, inten.): 280(17,M+), 193(19), 161(41), 135(40), 122(700, 104(69), 99(39),88(53), 78(65),71(100)

EXAMPLE 6

Preparation of 3-Chloro-2,2-dimethyl,5-(2,5-dimethylphenoxy) pentanoic Acid 2,2-Dimethyl-5-(2,5-dimethylphenoxy)-3-hydroxypentanoic Acid-$\beta$-lactone, 0.25 g(1 mmole), was dissolved in 30 ml of 1,4-dioxane. Dry hydrogen chloride gas was introduced and the resulting solution was stirred for 24 hours. The solution was concentrated in vacuo. The residue wwa dissolved in 100 ml of n-hexane, and washed with 100 ml of water. n-Hexane was evaporated and used again for recrystallization to give 0.25 g of the desired product, mp 117°–118° C. The yield was 85%.

PMR (80 MHz, CDCl$_3$); $\delta$7.90 (1H,s,—COOH); 7.00, 6.91 (1H, d,Ar—H); 6.66, 6.59(2H,d,Ar—H); 4.53(1H, dd, —CHCl —); 4.13(2H, g, Ar—O—CH$_2$—); 2.30(3H,s,Ar—CH$_3$); 2.16(3H,s,Ar—CH$_3$); 2.04(2H,m,Ar—O—CH$_2$—CH$_2$); 1.35 (6h, d——C(CH$_3$)$_2$—COO—).

Mass m/z (rel. inten.); 286 (9, M+2+), 284(15, M+), 248 (7), 204(11) 163(18), 147(11), 135(23), 121(46), 106(78). IR(KBr): 3026-2400(Broad), 1707 (vC=O—-COOH), 1614, 1585, 1551, 1510cm.

What is claimed is:

1. A compound having the formula (I):

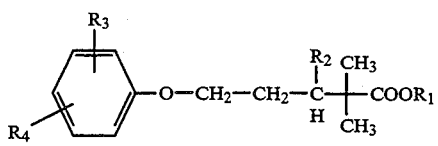

in which R$_1$ is hydrogen or C$_{1-8}$ alkyl;
R$_2$ is hydroxy or halogen; and
R$_3$ and R$_4$ are respectively hydrogen, hydroxy, halogen, C$_{1-8}$ alkyl, C$_{1-8}$ alkoxy or C$_{1-8}$ acyl.

2. The compound according to claim 1, 2,2-Dimethyl-5-(2,5-dimethylphenoxy)-3-hydroxypentanoic Acid.

3. The compound according to claim 1, Methyl 2,2-Dimethyl-5-(2,5-dimethylphenoxy)-3-hydroxy-pentanoate.

4. The compound according to claim 1, 3-chloro-2,2-dimethyl-5-(2,5-dimethylphenoxy)-pentanoic Acid.

5. A compound having the formula (II):

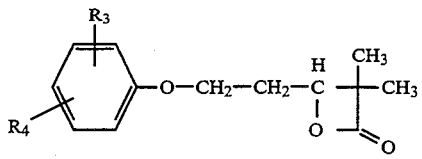

in which R$_3$ and R$_4$ are respectively hydrogen, hydroxy, halogen, C$_{1-8}$ alkyl, C$_{1-8}$ alkoxy or C$_{1-8}$ acyl.

6. The compound according to claim 5, 2,2-Dimethyl-5-(2,5-dimethylphenoxy)-3-hydroxy-pentanoic Acid $\beta$-lactone.

7. The compound according to claim 5, 5-(4-Chlorophenoxy)-2,2-dimethyl-3-hydroxypentanoic Acid $\beta$-Lactone.

8. A process for the preparation of compound having the formula (I):

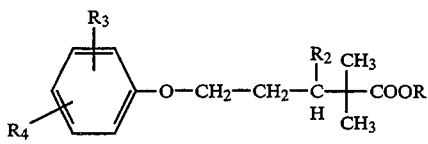

in which R$_1$ is hydrogen or C$_{1-8}$ alkyl;
R$_2$ is hydroxy or halogen; and
R$_3$ and R$_4$ are respectively hydrogen, hydroxy, halogen, C$_{1-8}$ alkyl, C$_{1-8}$ alkoxy or C$_{1-8}$ acyl;
comprising the step of reacting compound having formula (II)

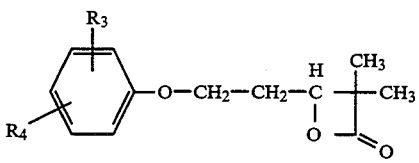

with a reagent selected from the group consisting of water, lower alkanol and hydrogen halide in a solvent selected from the group consisting of aliphatic alcohol and alkyl aromatics or in a polar aprotic solvent.

9. The process for the preparation of the compound having the formula (V)

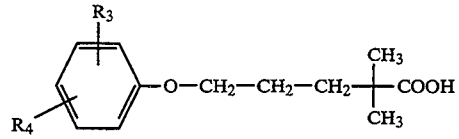

in which R$_3$ and R$_4$ are respectively hydrogen, hydroxy, halogen, C$_{1-8}$ alkyl, C$_{1-8}$ alkoxy or C$_{1-8}$ acyl, comprising the step of subjecting the compound of formula (II)

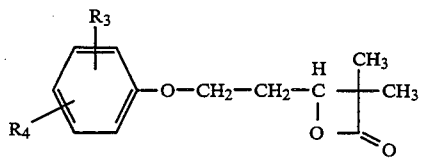

in which R$_3$ and R$_4$ are respectively hydrogen, hydroxy, halogen, C$_{1-8}$ alkyl, C$_{1-8}$ alkoxy or C$_{1-8}$ acyl, to hydrogenolysis in a polar protic solvent or polar aprotic solvent at a temperature of 20°-60° C. under 1-200 atm of hydrogen in the presence of a catalyst selected from the group consisting of Raney nickel, palladium/charcoal, and palladium hydroxide/charcoal.

10. The process as claimed in claim 9, wherein said compound (II) is 2,2-Dimethyl-5-(2,5-dimethylphenoxy)-3-hydroxy pentanoic Acid β-lactone, and said compound (V) is 2,2-Dimethyl-5-(2,5-dimethylphenoxy)-pentanoic Acid.

11. A process for the preparation of compound having the formula (II):

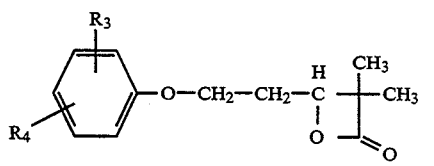 (II)

in which $R_3$ and $R_4$ are respectively hydrogen, hydroxy, halogen, $C_{1-8}$ alkyl, $C_{1-8}$ alkoxy or $C_{1-8}$ acyl, comprising the step of reacting a compound of the formula (III)

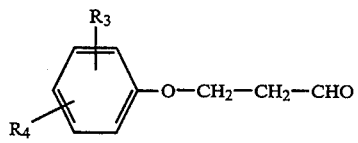

in which $R_3$ and $R_4$ are respectively hydrogen, hydroxy, halogen, $C_{1-8}$ alkyl, $C_{1-8}$ alkoxy or $C_{1-8}$ acyl, with dimethylketene of formula (IV)

 (IV)

in a nonpolar aprotic solvent or apolar aprotic solvent in the presence of a lewis acid.

12. The process as claimed in claim 11, wherein the compound (III) is 3-(2,5-Dimethylphenoxy)-propanal and the product compound (II) is 2,2-Dimethyl-5-(2,5-dimethylphenoxy)-3-hydroxy-pentanoic Acid β-lactone.

* * * * *